US010584616B2

(12) United States Patent
Moxon

(10) Patent No.: US 10,584,616 B2
(45) Date of Patent: Mar. 10, 2020

(54) CONTROL SYSTEM FOR SUPERCRITICAL WORKING FLUID TURBOMACHINERY

(71) Applicant: ROLLS-ROYCE PLC, London (GB)

(72) Inventor: Matthew Moxon, Derby (GB)

(73) Assignee: ROLLS-ROYCE plc, London (GB)

( * ) Notice: Subject to any disclaimer, the term of this patent is extended or adjusted under 35 U.S.C. 154(b) by 475 days.

(21) Appl. No.: 15/649,800

(22) Filed: Jul. 14, 2017

(65) Prior Publication Data

US 2018/0038245 A1 Feb. 8, 2018

(30) Foreign Application Priority Data

Aug. 5, 2016 (GB) .................................. 1613507.1

(51) Int. Cl.
*F01K 25/04* (2006.01)
*F02C 1/10* (2006.01)
(Continued)

(52) U.S. Cl.
CPC ................ *F01K 25/04* (2013.01); *F01K 7/00* (2013.01); *F01K 25/00* (2013.01); *F01K 25/103* (2013.01);
(Continued)

(58) Field of Classification Search
CPC .......... F01K 25/04; F01K 25/103; F01K 7/00; F01K 25/00; F02C 9/24; F02C 6/18; F02C 9/00; F02C 1/105; F02C 1/10; G01N 21/532; G01N 2021/0314; G01N 2021/8416; F05D 2270/804
See application file for complete search history.

(56) References Cited

U.S. PATENT DOCUMENTS

| 1,862,622 A | 6/1932 | Hoffman |
| 2014/0268158 A1 | 9/2014 | Tanriverdi |

(Continued)

FOREIGN PATENT DOCUMENTS

| CN | 1627063 A | 6/2005 |
| EP | 3109613 A1 | 12/2016 |
| JP | 2004-251746 A | 9/2004 |

OTHER PUBLICATIONS

Jan. 30, 2017 Search Report issued in British Patent Application No. 1613507.1.

(Continued)

*Primary Examiner* — Xiao En Mo
(74) *Attorney, Agent, or Firm* — Oliff PLC

(57) ABSTRACT

A turbomachinery control system for controlling supercritical working fluid turbomachinery. The control system includes a light emitter to project light through working fluid of the turbomachinery toward a primary light detector provided within a line of sight to the emitter. The system further includes one or more secondary light detectors spaced from the line of sight, and a controller determining one or both of an intensity of light detected by the primary detector relative to the detected light intensity by the secondary detector, and wavelength of light detected by the primary detector relative to wavelength of light detected by the secondary detector. The controller determines the working fluid proximity of the critical point based on one or both of the determined relative intensity and determined relative wavelength, and controlling an actuator to control turbomachinery inlet or outlet conditions in accordance with the working fluid determined proximity of the critical point.

12 Claims, 4 Drawing Sheets

(51) Int. Cl.
    *F01K 25/00* (2006.01)
    *F01K 7/00* (2006.01)
    *F02C 9/00* (2006.01)
    *F02C 6/18* (2006.01)
    *G01N 21/53* (2006.01)
    *F01K 25/10* (2006.01)
    *F02C 9/24* (2006.01)
    *G01N 21/84* (2006.01)
    *G01N 21/03* (2006.01)

(52) U.S. Cl.
    CPC .............. *F02C 1/10* (2013.01); *F02C 1/105* (2013.01); *F02C 6/18* (2013.01); *F02C 9/00* (2013.01); *F02C 9/24* (2013.01); *G01N 21/532* (2013.01); *F05D 2270/804* (2013.01); *G01N 2021/0314* (2013.01); *G01N 2021/8416* (2013.01)

(56) References Cited

U.S. PATENT DOCUMENTS

2014/0305170 A1  10/2014  Fetner et al.
2015/0101419 A1   4/2015  Hill et al.

OTHER PUBLICATIONS

Dec. 5, 2017 Search Report dated in European Patent Application No. 17181387.

Steven A. Wright et al. "Operation and Analysis of a Supercritical CO2 Brayton Cycle". Sandia Report SAND2010-0171, 2010, pp. 1-101.

V.G. Puglielli et al. "Turbidity Measurements in SF6 Near Its Critical Point". Physical Review Letters vol. 25 (3), 1970, pp. 143-147.

Robert M. Oag et al. "Determining Phase Boundaries and Vapour/Liquid Critical Points In Supercritical Fluids: A Multi-Technique Approach". The Journal of Supercritical Fluids, Elsevier, Amsterdam, NL, vol. 30, No. 3, 2004, pp. 259-272.

CONTROL SYSTEM FOR SUPERCRITICAL WORKING FLUID TURBOMACHINERY

The present disclosure concerns a control system for a turbine having a supercritical working fluid, and a method of controlling such a heat engine.

A supercritical fluid is any substance at a temperature and pressure above its critical point, where distinct liquid and gas phases do not exist. An example includes carbon dioxide ($CO_2$), for which the critical temperature and pressure are 304 K and 7.38 MPa respectively.

Turbines which operate on supercritical $CO_2$ working fluid as part of a closed Brayton or Rankine cycle heat engine have many advantages. In view of the high density and high temperatures of supercritical $CO_2$, extremely compact and high efficiency turbomachinery can be provided.

The present invention seeks to provide a method of controlling supercritical working fluid turbomachinery.

According to a first aspect there is provided a turbomachinery control system for controlling supercritical working fluid turbomachinery, the control system comprising:

a light emitter configured to project light through the working fluid toward a primary light detector provided within a line of sight to the emitter;

one or more secondary light detectors spaced from the line of sight;

a controller configured to determine one or both of an intensity of light detected by the primary detector relative to an intensity of light detected by the secondary detector, and a wavelength of light detected by the primary detector relative to a wavelength of light detected by the secondary detector;

the controller being configured to determine a proximity of the working fluid to a critical point based on one or both of the determined relative intensity and the determined relative wavelength, and to control an actuator configured to control turbomachinery inlet or outlet conditions in accordance with the determined proximity of the working fluid to the critical point.

Advantageously, the method of control can detect the proximity of the working fluid to the critical point by assessing the opalescence of the working fluid via one or both of the proportion of light detected by the secondary detectors relative to the first detectors, and the difference in wavelength of light detected by the secondary detectors relative to the first detectors. The secondary detectors are placed outside a line of sight to the primary detector, and therefore detect scattered light. Since supercritical working fluids undergo "critical opalescence" near the critical point, i.e. the fluid scatters light to a greater degree near to the critical point, the light sensed by the secondary sensor will differ in terms of one or more of intensity and wavelength relative to the light sensed by the primary sensor. Consequently, action can be taken to move the working fluid away from the critical point where necessary, thereby preventing damage to turbomachinery.

The control system may comprise a plurality of light sources configured to emit different wavelength light, and respective primary and secondary light detectors for each light source, the respective primary and secondary light detectors being configured to sense the wavelength emitted by the respective emitter.

The control system may comprise a plurality of spaced secondary light detectors. Advantageously, the spaced secondary light detectors can provide information regarding the distribution of temperature and pressure throughout the working fluid.

The emitter may comprise a monochromatic light source such as a laser, or a focused, broad spectrum light source such as an incandescent filament. Since the degree of scattering is related to the length scale of gaseous and liquid phase regions, which is in turn related to the proximity of the working fluid to the critical point, the wavelength of scattered light will vary in accordance with proximity to the critical point. Advantageously, where the light source is monochromatic, the intensity received by the secondary light detector relative to the primary light detector will vary greatly over a relatively small temperature and/or pressure variation. Alternatively, where the light source is broad spectrum, the colour of light received by the secondary sensor will provide improved measurement accuracy.

The control system may comprise a mirror in the light path between the emitter and the primary detector. Advantageously, increased sensitivity can be provided by increasing the length of the light path. Alternatively or in addition, the conditions of a larger volume of the working fluid can be assessed.

The controller may be configured to control the actuator to control one or more of the pressure and temperature of the working fluid, and the rotational speed and pressure ratio of the turbomachinery in accordance with the proximity of the working fluid to the critical point.

According to a second aspect of the invention there is provided a method for controlling supercritical working fluid turbomachinery, the method comprising:

projecting light from an emitter through working fluid of the turbomachinery toward a primary light detector provided within a direct line of sight to the emitter;

providing one or more secondary light detectors spaced from the primary detector;

determining one or both of:

an intensity of light detected by the primary detector relative to an intensity of light detected by the secondary detector; and a wavelength of light detected by the primary detector relative to a wavelength of light detected by the secondary detector;

determining a proximity of the working fluid to a critical point based on one or both of the determined relative intensity and the determined relative wavelength, and controlling turbomachinery inlet or outlet conditions in accordance with the determined proximity to the working fluid critical point.

According to a third aspect of the invention there is provided a turbomachine comprising a control system in accordance with the first aspect.

The turbomachine may comprise a closed Brayton cycle turbomachine comprising a compressor, heat exchanger and turbine arranged in flow series.

The closed Brayton cycle machine may comprise a heat recovery generator of an internal combustion engine.

The controller may be configured to modulate heat input into the heat recovery generator in accordance with proximity to the working fluid critical point. Advantageously, damage to the supercritical working fluid turbomachinery is prevented in the event of low pressure and/or temperature working fluid by shutting down the turbomachinery, by reducing heat input to the cycle.

The turbomachine may comprise an actuator controllable by the controller. The actuator may comprise one or more of a variable inlet and a variable outlet guide vane of one or more of the compressor and the turbine.

The skilled person will appreciate that except where mutually exclusive, a feature described in relation to any one of the above aspects may be applied mutatis mutandis to any other aspect. Furthermore except where mutually exclusive any feature described herein may be applied to any aspect and/or combined with any other feature described herein.

Embodiments will now be described by way of example only, with reference to the Figures, in which.

Figure 1:
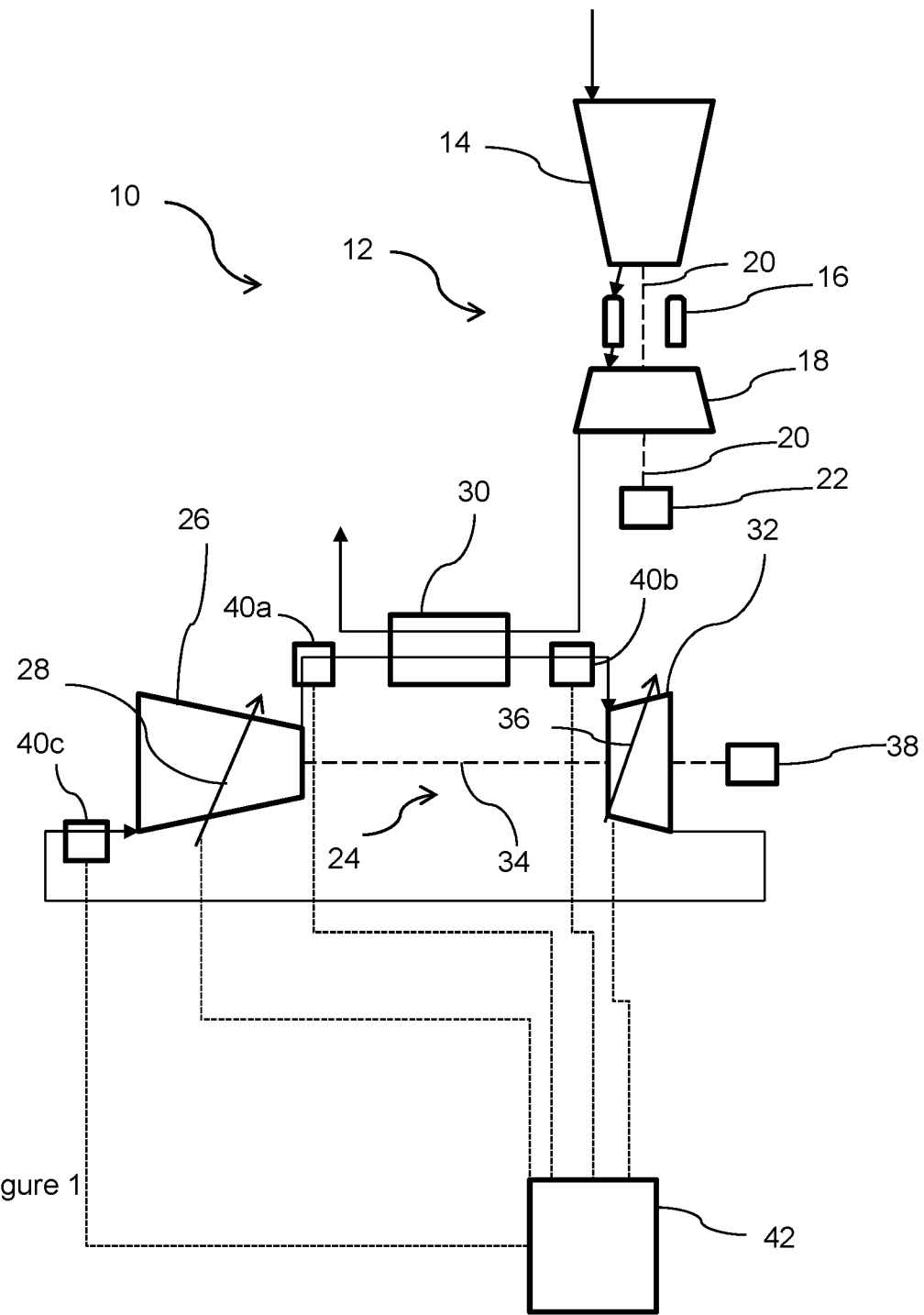
FIG. 1 is a schematic representation of a gas turbine engine comprising a heat recovery turbomachine.
Figure 2:
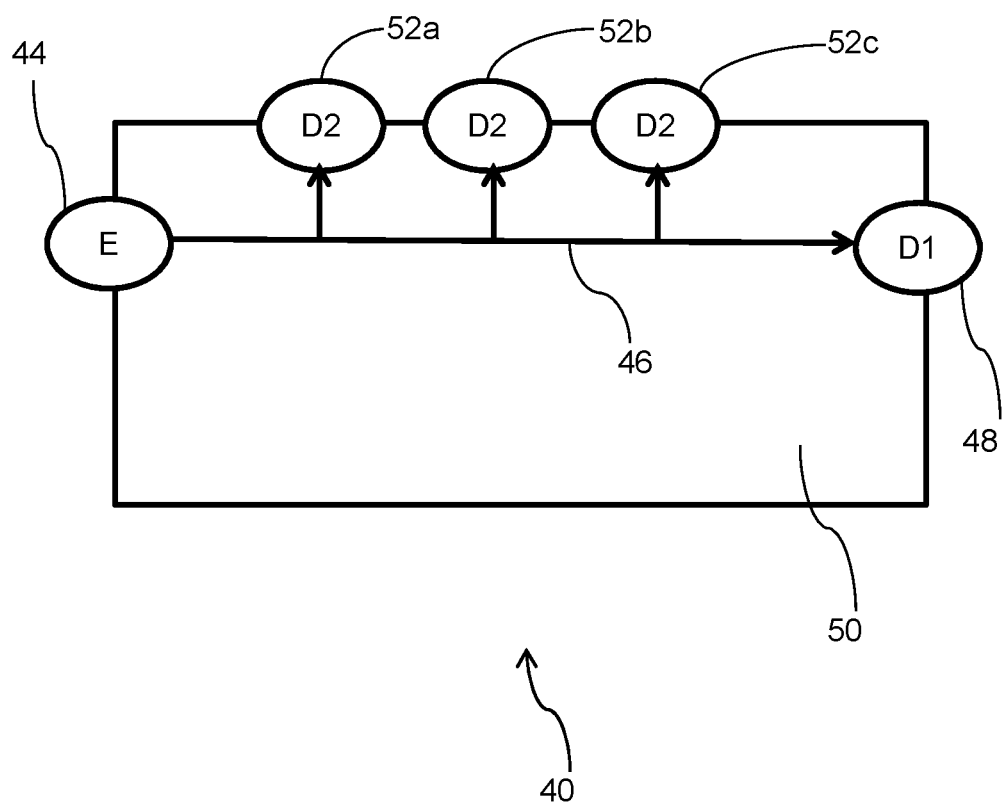
FIG. 2 is a schematic representation of part of a control system for the heat recovery turbomachine of FIG. 1.

Referring to FIGS. 1 and 2, there is shown a power generation system 10 comprising a gas turbine engine 12 and a heat recovery turbomachine 24 which operates on a supercritical working fluid such as supercritical carbon dioxide.

The gas turbine engine 12 comprises an air compressor 14 configured to ingest atmospheric air and pressurise air for delivery to a combustor 16. The combustor is configured to combust the compressed air with fuel provided by fuel injectors (not shown), and deliver hot combustion products to a turbine 18 provided downstream. The turbine 18 is configured to expand the hot combustion products, and thereby turn a shaft 20 coupled thereto. The compressor 14 is also coupled to the shaft 20, such that rotation of the shaft 20 drives the compressor 14. The shaft is also generally configured to drive a load 22 such as an electrical generator, fan, marine propeller etc.

Exhaust gasses from the turbine 18 are generally still of a relatively high temperature, and so it is desirable to recover heat therefrom to increase system thermal efficiency. Consequently, the power generation system 10 further comprises a heat recovery power generation turbomachine 24.

The heat recovery power generation turbomachine 24 is in the form of a closed Brayton cycle turbomachine. The turbomachine 24 comprises a variable geometry compressor 26 configured to compress the working fluid. The variable geometry compressor may be of any suitable type, such as a centrifugal or axial compressor. The compressor 26 may be configured to operate on the working fluid as a sub-critical compressible gas, or as a compressible supercritical fluid. Typically, the variable geometry compressor comprises at least one actuator 28 configured to change inlet or outlet area. For example, the compressor may comprise actuators in the form of variable inlet guide vanes, which are operable to vary the inlet area to the compressor 26, and may comprise an actuator in the form of variable diffuser guide vanes operable to vary the outlet area of the compressor. Consequently, one or more of flow rate, pressure ratio, temperature and volume can be controlled independently of compressor rotational speed. Consequently, the pressure and temperature of working fluid upstream and downstream of the compressor 28 can be controlled.

The heat recovery turbomachine 24 further comprises a heat exchanger 30. The heat exchanger 30 is configured to exchange heat from the gas turbine engine 12 exhaust gasses downstream of the turbine 18 to the working fluid of the heat recovery turbomachine downstream of the compressor 26, and upstream of a turbine 32, to thereby heat the working fluid. The heat exchanger 30 is shown as counter flow, through it will be understood that co-flow and cross-flow configurations are also suitable. Suitable heat exchangers include shell and tube type and plate fin heat exchangers.

Again, the heat exchanger 30 may comprise an actuator configured to control one or more of pressure drop, flow rate and heat exchanger. For example, the heat exchanger may comprise a bypass passage configured to bypass working fluid flow around heat exchange elements, thereby reducing heat input to the working fluid 30. The actuator may comprise a valve configured to control flow through the heat exchange elements and the bypass passage.

The turbine 32 is provided downstream of the heat exchanger in working fluid flow. The turbine 32 is configured to expand the working fluid in a similar manner to the turbine 18 of the gas turbine engine 12, and to provide shaft power to a shaft 34. Again, the turbine 32 could be of any conventional type, including centrifugal and axial, and is of a variable geometry type. Typically, the variable geometry turbine 32 comprises at least one actuator 36 configured to change inlet or outlet area. For example, the turbine 32 may comprise actuators in the form of variable inlet guide vanes, which are operable to vary the inlet area to the turbine 32, and may comprise an actuator in the form of variable diffuser guide vanes operable to vary the outlet area of the turbine 32. Consequently, one or more of flow rate, pressure ratio, temperature and volume can be controlled independently of turbine 32 rotational speed. Consequently, the pressure and temperature of working fluid upstream and downstream of the turbine 32 can be controlled. Again, the turbine 32 is configured to operate on either gaseous or supercritical working fluid. Preferably though, the turbine can be made smaller and more efficient where the working fluid is maintained as a supercritical fluid during operation of the turbine.

An outlet of the turbine 32 is in fluid communication with an inlet of the compressor 26, such that the turbomachine 24 is closed loop. The shaft 34 is coupled to both the turbine 32 and compressor 26 such that rotation of the turbine 32 drives the compressor 26. Again, a shaft driven load 38 is provided.

In operation, the gas turbine engine is operated such that air flows in through the compressor 14 where it is heated and compressed, the combustor 16 where it is further heated, and the turbine 18 where it is expanded and cooled, though to a temperature greater than the temperature of intake air. Waste heat from the turbine 18 is transferred to the heat recovery turbomachine 24 via the heat exchanger 30, which thereby heats the working fluid. The heated working fluid is expanded and cooled by the turbine 32, before being passed to the compressor 26 which compresses the working fluid before delivery back to the heat exchanger 30, thereby closing the loop.

It will be understood that the amount of heat transferred to the working fluid of the heat recovery turbomachine 24 will vary in accordance with combustor input heat, air inlet temperature, turbine efficiency, and, where present, heat exchanger bypass operation. Consequently, the temperature of the working fluid downstream of the heat exchanger will vary in operation. Consequently, the temperature of working fluid upstream of the turbine will vary, which will affect turbine efficiency, expansion ratio and rotational speed. Consequently, compressor inlet and outlet pressure and temperature will vary in accordance with the temperature of working fluid delivered to the compressor, and will also vary in accordance with shaft rotational speed as determined by turbine rotational speed. These parameters will all evolve over time due to continually changing inlet conditions and system lag.

The working fluid will therefore vary in temperature at all points in the cycle (particularly compressor inlet and outlet pressures and temperatures, heat exchanger inlet and outlet pressures and temperatures and turbine inlet and outlet pressures and temperatures). Accordingly, the working fluid may be above or below the critical point for the working fluid, and so may be a gas, a liquid, a supercritical fluid, or a mixture thereof. Where the working fluid is above the critical point (i.e. is supercritical), the proximity to the critical point (i.e. how far above the critical point the temperature and pressure of the working fluid is) will determine properties of the working fluid such as density and compressibility. In general, for turbomachinery configured to operate on supercritical working fluid, it is desirable for the working fluid to be maintained above the critical point, and preferably well above the critical point. Alternatively, where operation close to the critical point is unavoidable, it may be desirable to control the turbomachinery (i.e. the compressor 26 and turbine 32) accordingly. Consequently, a control arrangement is provided for controlling one or more actuators 28, 36 of the supercritical working fluid turbomachinery in accordance with a sensed proximity to the critical point.

The control arrangement comprises one or more critical opalescence sensor arrays 40a-c. Each array is located to sense proximity of the working fluid to the critical point at a different point in the cycle. For instance, in the described embodiment, a first sensor array 40a is configured to sense proximity of working fluid downstream of the compressor 26 and upstream of the heat exchanger 30, a second sensor array 40b is configured to sense proximity of working fluid downstream of the heat exchanger 30 and upstream of the turbine 32, and a third sensor array 40c is configured to sense proximity of working fluid downstream of the turbine 32 and upstream of the compressor 26. Each sensor array 40a-c is in signal communication with a controller 42. The controller 42 is in signal communication with each actuator 28, 36 and so is configured to control the actuators 28, 36 in accordance with a critical point proximity of the working fluid as sensed by each sensor array 40a-c.

A sensor array 40 is shown in more detail in FIG. 2. The array comprises a broad spectrum light emitter in the form of an incandescent light 44. The incandescent light is configured to provide a beam of light 46 which is directed toward a primary detector 48, provided within line of sight of the emitter 44, the beam of light 46 being transmitted directly through the working fluid 50 at a point of interest in the heat recovery cycle. A plurality of secondary detectors 52a, 52b, 52c are also provided. Each secondary detector is provided spaced from the line of sight of the emitter 44, i.e. the beam 46 is not directed toward the secondary detectors 52a-c, such that the secondary detectors 52a-c substantially only receive scattered light via the working fluid, rather than direct light.

Each of the secondary detectors 52a-c is spaced relative to the other secondary detectors. In particular, each secondary detector 52a-c is provided at a different angular position relative to the other sensors 52a-c and relative to the beam of light 46. In the example shown, sensor 52c is provided at a smaller angle relative to the line of sight of the beam 46 than the sensors 52b, 52a. Consequently, the sensors 52a-c may be used to detect working fluid conditions at different points along the length of the beam 46. Furthermore, the provision of multiple secondary detectors provides redundancy.

Figure 4:
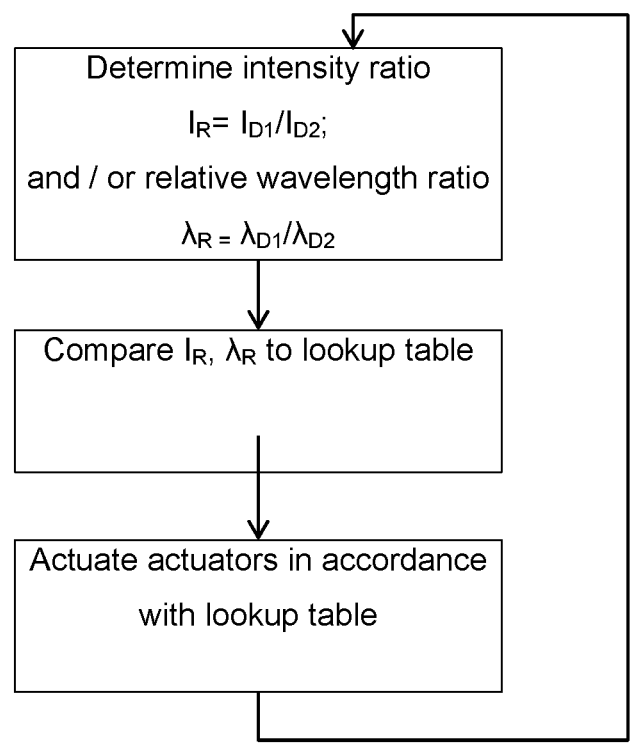
FIG. 4 is a flow diagram of a method of controlling the heat recovery turbomachine of FIG. 1.

Referring now to FIG. 4, the controller 42 controls the turbomachinery 24 as follows.

In a first step, light is emitted by the emitter 44 and absorbed by the primary and secondary detectors 48, 52. An opalescence of the working fluid is determined by the ratio of light detected by the primary detector 48 relative to the secondary detectors 52a-c. Individual opalescences may be calculated for different points in the fluid 50 by calculating three separate ratios (one for each secondary detector) or an average of the three secondary detectors may be taken to determine a single ratio. In general, a lower ratio will be indicated of more scattering of light from the emitter, and so higher opalescence. Consequently, where the ratio is low, it can be determined that the working fluid 50 is close to the critical point, i.e. at least one of the temperature and pressure is close to the critical point.

In a second step, the ratio is compared to a predetermined value, or to a lookup table relating actuator positions to the ratio.

In a third step, the controller controls the actuator to move the working fluid away from the critical point, e.g. the controller 42 positions the actuator in accordance with the lookup table, or a to a position which moves the ratio above the predetermined ratio. For example, where the ratio determined by the sensor array 40b determines that the working fluid at this point is close to the critical point, the controller 42 actuates the variable geometry turbine actuator 36 to reduce the area of the turbine outlet (e.g. to close the variable outlet guide vanes) to thereby reduce the expansion ratio of the turbine, and so raise the pressure and temperature of the working fluid downstream of the turbine 32, thereby maintaining the working fluid as a critical working fluid. Alternatively, or in addition, the load on the shaft 34 may be reduced. This can be achieved by utilising the compressor actuator 28 to reduce the pressure ratio of the compressor 26 be increasing the outlet area or increasing the inlet area of the compressor 26. Alternatively, the load 38 could be modulated to reduce the shaft load. As a still further alternative, the heat input to the turbomachine 24 could be increased by closing the heat exchanger bypass valve, or by increasing fuel flow to the gas turbine engine combustor 16.

Similar action could be taken where the supercritical working fluid is found to be close to or below the critical point in other points of the cycle.

The method is repeated, to provide continual monitoring of the proximity of the working fluid to the critical point, and to adjust the turbomachinery accordingly.

Figure 3:
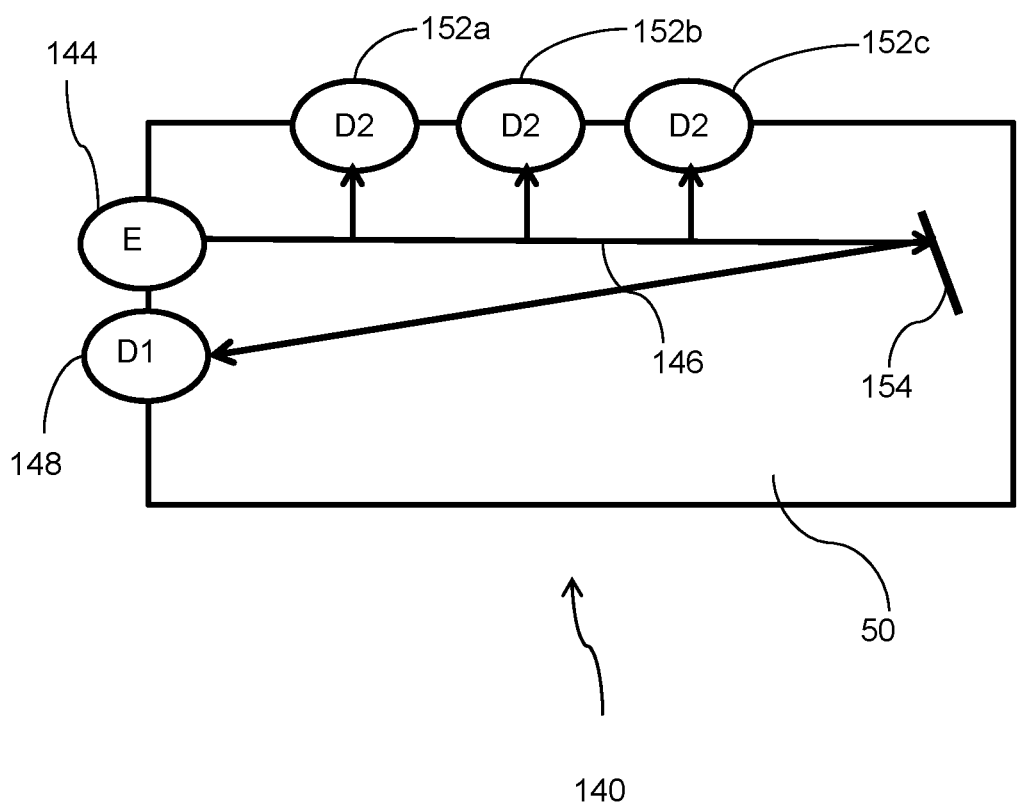
FIG. 3 is a schematic representation of part of an alternative control system for the heat recovery turbomachine of FIG. 1.

FIG. 3 shows an alternative sensor array 140 for the turbomachine 24 of FIG. 1. The array 140 again comprises an emitter 144, which produces a broad spectrum light beam 146. The beam 146 is directed toward a mirror 154, which reflects the beam toward a primary detector 148. Consequently, the length of the beam 146 is increased relative to the first embodiment, which increases the sensitivity of the detector, and ensures that the conditions of a larger proportion of the working fluid 50 are sensed.

Secondary detectors 152a-c are again provided out of the line of sight of the emitter 144, and so detect scattered light. The detectors 152a-c are each configured to sense different wavelength light (i.e. different colours). Scattering is caused when the size of density variations of the working fluid 50 approaches the wavelength of the light. Consequently, the different secondary detectors 152a-c can determine the size of the density variations of the working fluid 50, and thereby providing an indication of proximity to the critical point. Furthermore, the secondary detectors 152a-c may also detect the intensity of the scattered, light as in the previously described embodiment.

Furthermore, in general, where a board spectrum light source is employed, short wavelength light will tend to be preferentially scattered. Consequently, the secondary detectors 152a-c will detect light which is "bluer" than that detected by the primary detector 148, which is in turn "redder" than the emitted light from the emitter 144. Consequently, the relative wavelengths detected by the primary 148 and secondary 152 detectors can be used by the controller 42 as an indication of proximity to the critical point, as an alternative to, or in addition to, a comparison of the relative intensities of the light received by the detectors 148, 152. For example, where the ratio $\lambda_R$ of wavelengths detected by the primary and secondary detectors 148, 152 is approximately 1, then the working fluid can be deduced to be well above the critical point. Conversely, where the ratio of wavelengths is less than 1, then it can be deduced that the working fluid 50 is close to the critical point. In one example, the measurement of the proximity of the working fluid to the critical point using the relative wavelengths method and the relative intensities method can be combined, with the actuators being controlled on the basis of an average of the two methods.

It will be understood that the invention is not limited to the embodiments above-described and various modifications and improvements can be made without departing from the concepts described herein. Except where mutually exclusive, any of the features may be employed separately or in combination with any other features and the disclosure extends to and includes all combinations and sub-combinations of one or more features described herein.

For example, the light does not have to be visible light, and could for example comprise ultraviolet or infrared light, or electromagnetic radiation of longer or shorter wavelengths. The working fluid could comprise other supercritical working fluids, such as steam. The turbomachinery could comprise different types of compressor and/or turbines. The turbomachinery could be open cycle, and could comprise an open cycle Brayton cycle or Rankine cycle. The turbomachinery could be recuperated and/or intercooled, and could comprise multiple stages of compression and expansion. Multiple compressors and turbine could be provided, which could be interconnected by independent shafts.

The invention claimed is:

1. A turbomachinery control system for controlling supercritical working fluid turbomachinery, the control system comprising:
   a light emitter configured to project light through working fluid of the turbomachinery toward a primary light detector provided within a line of sight to the emitter;
   one or more secondary light detectors spaced from the line of sight;
   a controller configured to determine one or both of an intensity of light detected by the primary detector relative to an intensity of light detected by the secondary detector, and a wavelength of light detected by the primary detector relative to a wavelength of light detected by the secondary detector;
   the controller being configured to determine a proximity of the working fluid to a critical point based on one or both of the determined relative intensity and the determined relative wavelength, and to control an actuator configured to control turbomachinery inlet or outlet conditions in accordance with the determined proximity of the working fluid to the critical point.

2. The system according to claim 1, wherein the control system comprises plurality of light sources configured to emit different wavelength light, and respective primary and secondary light detectors for each light source, the respective primary and secondary light detectors being configured to sense the wavelength emitted by the respective emitter.

3. The system according to claim 1, wherein the control system comprises a plurality of spaced secondary light detectors.

4. The system according to claim 1, wherein the emitter comprises one of a monochromatic light source such as a laser, and a focused, broad spectrum light source such as an incandescent filament.

5. The system according to claim 1, wherein the control system comprises a mirror in the light path between the emitter and the primary detector.

6. The system according to claim 1, wherein the controller is configured to control the actuator to control one or more of the pressure and temperature of the working fluid, and the rotational speed and pressure ratio of the turbomachinery in accordance with the proximity of the working fluid to the critical point.

7. A method for controlling supercritical working fluid turbomachinery, the method comprising:
   projecting light from an emitter through working fluid of the turbomachinery toward a primary light detector provided within a direct line of sight to the emitter;
   providing one or more secondary light detectors spaced from the line of sight;
   determining one or both of:
   an intensity of light detected by the primary detector relative to an intensity of light detected by the secondary detector; and
   a wavelength of light detected by the primary detector relative to a wavelength of light detected by the secondary detector;
   determining a proximity of the working fluid to a critical point based on one or both of the determined relative intensity and the determined relative wavelength; and
   controlling turbomachinery inlet or outlet conditions in accordance with the determined proximity to the working fluid critical point.

8. A turbomachine comprising the control system according to claim 1.

9. The turbomachine according to claim 8, wherein the turbomachine comprises a closed Brayton cycle turbomachine comprising a compressor, heat exchanger and turbine arranged in flow series.

10. The turbomachine according to claim 9, wherein the closed Brayton cycle machine comprised a heat recovery generator of an internal combustion engine.

11. The turbomachine according to claim 9, wherein the controller is configured to modulate heat input into the heat recovery generator in accordance with proximity to the working fluid critical point.

12. The turbomachine according to claim 8, wherein the turbomachine comprises an actuator controllable by the controller, The actuator comprising one or more of a variable inlet and a variable outlet guide vane of one or more of the compressor and the turbine.

* * * * *